United States Patent
Malina

(10) Patent No.: US 8,778,349 B2
(45) Date of Patent: Jul. 15, 2014

(54) MODIFICATION OF INTRINSICALLY DISORDERED SEQUENCES FOR THE PREPARATION OF VACCINES

(76) Inventor: Halina Malina, Les Ulis (FR)

( * ) Notice: Subject to any disclaimer, the term of this patent is extended or adjusted under 35 U.S.C. 154(b) by 915 days.

(21) Appl. No.: 12/739,481

(22) PCT Filed: Oct. 30, 2008

(86) PCT No.: PCT/FR2008/001527
§ 371 (c)(1),
(2), (4) Date: Apr. 23, 2010

(87) PCT Pub. No.: WO2009/092891
PCT Pub. Date: Jul. 30, 2009

(65) Prior Publication Data
US 2010/0303844 A1     Dec. 2, 2010

(30) Foreign Application Priority Data
Oct. 31, 2007 (FR) ...................................... 07 07646

(51) Int. Cl.
| | | |
|---|---|---|
| A61K 39/00 | (2006.01) | |
| A61K 39/395 | (2006.01) | |
| A61K 38/00 | (2006.01) | |
| C12N 15/00 | (2006.01) | |
| C07K 16/00 | (2006.01) | |
| C12N 7/00 | (2006.01) | |
| C07K 7/08 | (2006.01) | |
| C07K 7/06 | (2006.01) | |
| C07K 14/47 | (2006.01) | |

(52) U.S. Cl.
CPC . *C07K 14/47* (2013.01); *C07K 7/08* (2013.01); *C07K 7/06* (2013.01); *A61K 38/00* (2013.01)
USPC ..................... 424/184.1; 424/194.1; 435/326; 435/449; 530/390.5; 530/391.5; 530/391.9

(58) Field of Classification Search
None
See application file for complete search history.

(56) References Cited

U.S. PATENT DOCUMENTS

| | | | |
|---|---|---|---|
| 5,275,814 A * | 1/1994 | Wojdani ................... | 424/195.11 |
| 5,302,386 A * | 4/1994 | Kasper et al. ............ | 424/197.11 |
| 2003/0139324 A1* | 7/2003 | Steck et al. ........................ | 514/2 |
| 2005/0186657 A1* | 8/2005 | Schultz et al. ............... | 435/68.1 |
| 2012/0190823 A1* | 7/2012 | Santner et al. ................ | 530/350 |
| 2013/0059338 A1* | 3/2013 | Santner et al. ............... | 435/69.7 |

FOREIGN PATENT DOCUMENTS

| | | | |
|---|---|---|---|
| WO | WO 0058344 | * 10/2000 | |

OTHER PUBLICATIONS

Skrabana et al. Azlheimer's-disease-associated conformation of intrinsically disordered tau protein studied by intrinsically disordered protein liquid-phase competitive enzyme-linked immunosorbent assay. Analytical Biochemistry 359:230-237 (Oct. 19, 2006).*
Saroja et al. Recent Trends in vaccine delivery systems: A review. Internal Journal of Pharmaceutical Investigation vol. 1/2:64-74 (Apr. 2011).*
English translation of document WO 00/58344 (Oct. 5, 2000).*
Malina et al. Xanthurenic acid changes signaling of 14-3-3 proteins and calmodulin: Involvement in the diseases development and drug targeting. Abstract. IOVS, vol. 46, No. Suppl. S, pp. 5291. Meeting Info.: Annual Meeting of the Association-for-Research-in-Vision-and-Ophthalmology. Ft Lauderdale, FL (2005).*
Prilusky et al. FoldIndex: a simple tool to predict whether a given protein sequence is intrinsiically unfolded. Bioinformatics vol. 21, No. 16 pp. 3435-3438 (Jun. 2005).*
Uversky, V. N. What does it mean to be natively unfolded? Eur. J. Biochem. vol. 269 pp. 2-12 (2002).*
Dedmon et al. FlgM gains structure in living cells, PNAS vol. 99/20:12681-12684 (2002).*
Bingham et al. Crystal structures of fibronectin-binding sites from *Staphylococcus aureus* FnBPA in complex with fibronectin domains, PNAS vol. 105/34:12254-12258 (Aug. 2008).*
Uversky et al. Showing your ID: intrinsic disorder as an ID for recognition, regulation and cell signaling, Journal of Molecular Recognition, vol. 18:343-384 (2005).*
Dunker et al. Intrinsic Disorder and Protein Function Biochemistry vol. 41/21:6574-6582 (2002).*
Scheuermann et al. Homodimerization of Amyloid Precursor Protein and Its Implication in the Amyloidogenic Pathway of Alzheimer's Disease. J. Biol. Chem. 2001, 276:33923-33929 (Jul. 2001).*

* cited by examiner

*Primary Examiner* — Elizabeth C Kemmerer
*Assistant Examiner* — Regina M Deberry

(57) ABSTRACT

The intrinsically disordered sequences—or "intrinsically disorded sequences" or IDSeq—proteins should be flexible to ensure a controlled interaction between proteins. In the development of the diseases, IDSeq are modified and polymerized. The invention describes the method of preparation of the drugs against cancers, the degenerative diseases and the infectious illness, by the induction of an immune reaction against IDSeq modified in a covalent way (IDSeqC) and polymerized (pIDSeqC), and leading to a new network of protein signaling, named here "misfoldome", causing the diseases. The invention describes the preparation of vaccines by the use of polymers of IDSeqC. Peptides of the pIDSeqC are prepared in vitro, and introduced into a living organism to induce an immunological response, which eliminates the "misfoldome" and cures the diseases. The method is employed for the preparation of active or passive vaccines. The technology is adapted to detect, prevent or cure the diseases associated with ageing such as the degenerative diseases, cancers, and infections.

5 Claims, No Drawings

SEQUENCE LISTING

<160> NUMBER OF SEQ ID NOS: 58

<210> SEQ ID NO 1
<211> LENGTH: 32
<212> TYPE: PRT
<213> ORGANISM: Homo sapiens

<400> SEQUENCE: 1

Asn Lys Glu Tyr Gly Ser Glu Lys Lys Gly Tyr Leu Leu Lys Lys Ser
1               5                   10                  15

Asp Gly Ile Arg Lys Val Trp Gln Arg Arg Lys Cys Ser Val Lys Asn
            20                  25                  30

<210> SEQ ID NO 2
<211> LENGTH: 20
<212> TYPE: PRT
<213> ORGANISM: Homo sapiens

<400> SEQUENCE: 2

Leu Val Leu Arg Arg Lys Arg Lys Arg Met Thr Asp Pro Thr Arg Arg
1               5                   10                  15

Phe Phe Lys Val
            20

<210> SEQ ID NO 3
<211> LENGTH: 35
<212> TYPE: PRT
<213> ORGANISM: Homo sapiens

<400> SEQUENCE: 3

Asn Lys Glu Tyr Gly Ser Glu Lys Lys Gly Tyr Leu Leu Lys Lys Ser
1               5                   10                  15

Asp Gly Ile Arg Lys Val Trp Gln Arg Arg Lys Cys Ser Val Lys Asn
            20                  25                  30

Gly Ile Leu
        35

<210> SEQ ID NO 4
<211> LENGTH: 11
<212> TYPE: PRT
<213> ORGANISM: Homo sapiens

<400> SEQUENCE: 4

Thr Lys Lys Phe Gly Trp Val Lys Lys Tyr Val
1               5                   10

<210> SEQ ID NO 5
<211> LENGTH: 8
<212> TYPE: PRT
<213> ORGANISM: Homo sapiens

<400> SEQUENCE: 5

Val Lys Lys Ile Pro Lys Lys Pro
1               5

<210> SEQ ID NO 6
<211> LENGTH: 16
<212> TYPE: PRT
<213> ORGANISM: Homo sapiens

<400> SEQUENCE: 6

Phe His Lys Gln Asn Lys Met Leu Lys Lys Asp Lys Met Phe His Phe
1               5                   10                  15

```
<210> SEQ ID NO 7
<211> LENGTH: 14
<212> TYPE: PRT
<213> ORGANISM: Homo sapiens

<400> SEQUENCE: 7

Arg Asp Ile Tyr Glu Thr Asp Tyr Tyr Arg Lys Gly Gly Lys
1               5                   10

<210> SEQ ID NO 8
<211> LENGTH: 93
<212> TYPE: PRT
<213> ORGANISM: Homo sapiens

<400> SEQUENCE: 8

Asn Cys Gln Lys Leu Thr Lys Ile Ile Cys Ala Gln Gln Cys Ser Gly
1               5                   10                  15

Arg Cys Arg Gly Lys Ser Pro Ser Asp Cys Cys His Asn Gln Cys Ala
            20                  25                  30

Ala Gly Cys Thr Gly Pro Arg Glu Ser Asp Cys Leu Val Cys Arg Lys
        35                  40                  45

Phe Arg Asp Glu Ala Thr Cys Lys Asp Thr Cys Pro Pro Leu Met Leu
50                  55                  60

Tyr Asn Pro Thr Thr Tyr Gln Met Asp Val Asn Pro Glu Gly Lys Tyr
65                  70                  75                  80

Ser Phe Gly Ala Thr Cys Val Lys Lys Cys Pro Arg Asn
                85                  90

<210> SEQ ID NO 9
<211> LENGTH: 27
<212> TYPE: PRT
<213> ORGANISM: Homo sapiens

<400> SEQUENCE: 9

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala
            20                  25

<210> SEQ ID NO 10
<211> LENGTH: 21
<212> TYPE: PRT
<213> ORGANISM: Homo sapiens

<400> SEQUENCE: 10

Glu Lys Lys Ile Glu Met Val Arg Ala Tyr Arg Glu Lys Ile Glu Lys
1               5                   10                  15

Glu Leu Glu Ala Val
            20

<210> SEQ ID NO 11
<211> LENGTH: 10
<212> TYPE: PRT
<213> ORGANISM: Homo sapiens

<400> SEQUENCE: 11

Phe Lys Ser Gly Leu Lys Tyr Lys Lys Gly
1               5                   10

<210> SEQ ID NO 12
```

```
<211> LENGTH: 22
<212> TYPE: PRT
<213> ORGANISM: Homo sapiens

<400> SEQUENCE: 12

Val Arg Phe Leu Asp Lys Lys His Arg Asn His Tyr Arg Val Tyr Asn
1               5                   10                  15

Leu Cys Ser Glu Arg Ala
            20

<210> SEQ ID NO 13
<211> LENGTH: 15
<212> TYPE: PRT
<213> ORGANISM: Homo sapiens

<400> SEQUENCE: 13

Trp Cys Lys Arg Gly Arg Lys Gln Cys Lys Thr His Pro His Phe
1               5                   10                  15

<210> SEQ ID NO 14
<211> LENGTH: 23
<212> TYPE: PRT
<213> ORGANISM: Homo sapiens

<400> SEQUENCE: 14

Phe Gln Lys Ala Lys Glu Arg Leu Glu Ala Lys His Arg Glu Arg Met
1               5                   10                  15

Ser Gln Val Met Arg Glu Trp
            20

<210> SEQ ID NO 15
<211> LENGTH: 22
<212> TYPE: PRT
<213> ORGANISM: Homo sapiens

<400> SEQUENCE: 15

Ala Lys Ala Asp Lys Ile Lys Leu Ala Leu Glu Lys Leu Lys Glu Ala
1               5                   10                  15

Lys Val Lys Lys Leu Val
            20

<210> SEQ ID NO 16
<211> LENGTH: 43
<212> TYPE: PRT
<213> ORGANISM: Homo sapiens

<400> SEQUENCE: 16

Ala Leu Lys Lys Tyr Gln Thr Glu Gln Arg Ser Lys Gly Asp Ala Leu
1               5                   10                  15

Asp Lys Cys Gln Ala Glu Leu Lys Lys Leu Arg Lys Lys Ser Gln Gly
            20                  25                  30

Ser Lys Asn Pro Gln Lys Tyr Ser Asp Lys Glu
            35                  40

<210> SEQ ID NO 17
<211> LENGTH: 12
<212> TYPE: PRT
<213> ORGANISM: Homo sapiens

<400> SEQUENCE: 17

Asn Arg Lys Asp Phe Lys Ile Asp Arg Lys Lys Ala
1               5                   10
```

```
<210> SEQ ID NO 18
<211> LENGTH: 10
<212> TYPE: PRT
<213> ORGANISM: Homo sapiens

<400> SEQUENCE: 18

Pro Val Lys Lys Arg Lys Arg Lys Cys Leu
1               5                   10

<210> SEQ ID NO 19
<211> LENGTH: 31
<212> TYPE: PRT
<213> ORGANISM: Homo sapiens

<400> SEQUENCE: 19

Thr Arg Leu Phe Gly Leu Thr Lys Pro Lys Glu Lys Lys Glu Lys Lys
1               5                   10                  15

Lys Lys Asn Lys Thr Ser Arg Ser Gln Pro Gly Asp Gly Pro Ala
            20                  25                  30

<210> SEQ ID NO 20
<211> LENGTH: 46
<212> TYPE: PRT
<213> ORGANISM: Homo sapiens

<400> SEQUENCE: 20

Phe Ser Tyr Ile Lys Asn Lys Met Ser Ser Lys Ser Lys Glu
1               5                   10                  15

Lys Glu Lys Glu Lys Asp Lys Ile Lys Glu Lys Glu Lys Asp Ser Lys
            20                  25                  30

Asp Lys Glu Lys Asp Lys Lys Thr Val Asn Gly His Thr Phe
        35                  40                  45

<210> SEQ ID NO 21
<211> LENGTH: 18
<212> TYPE: PRT
<213> ORGANISM: Homo sapiens

<400> SEQUENCE: 21

Asn Thr Asp Arg Ser Cys Arg Lys Lys Asn Lys Gly Val Glu Arg Lys
1               5                   10                  15

Gly Glu

<210> SEQ ID NO 22
<211> LENGTH: 38
<212> TYPE: PRT
<213> ORGANISM: Homo sapiens

<400> SEQUENCE: 22

Ala Ser Val Ser Ser Gly Arg Lys Ser Pro His Ser Lys Ser Pro Ala
1               5                   10                  15

Glu Gln Arg Glu Arg Lys Ser Leu Ala Asp Lys Lys Lys Val Lys
            20                  25                  30

Asn Leu Gly Tyr Arg Asp
        35

<210> SEQ ID NO 23
<211> LENGTH: 20
<212> TYPE: PRT
<213> ORGANISM: Homo sapiens

<400> SEQUENCE: 23
```

```
Glu Glu Ser Arg Val Arg Arg His Lys His Ser Ser Glu Ser Pro Gly
1               5                   10                  15

Arg Asp Lys Gly
            20

<210> SEQ ID NO 24
<211> LENGTH: 7
<212> TYPE: PRT
<213> ORGANISM: Homo sapiens

<400> SEQUENCE: 24

Phe Leu Arg Arg Lys Arg Asp
1               5

<210> SEQ ID NO 25
<211> LENGTH: 11
<212> TYPE: PRT
<213> ORGANISM: Homo sapiens

<400> SEQUENCE: 25

Ala Arg Lys Glu Lys Lys Gly Lys His Lys Gly
1               5                   10

<210> SEQ ID NO 26
<211> LENGTH: 11
<212> TYPE: PRT
<213> ORGANISM: Homo sapiens

<400> SEQUENCE: 26

Asn Lys Gln Asn Gln Lys Lys Arg Lys Val
1               5                   10

<210> SEQ ID NO 27
<211> LENGTH: 15
<212> TYPE: PRT
<213> ORGANISM: Homo sapiens

<400> SEQUENCE: 27

Glu Arg Glu Arg Ala Arg Arg Arg Glu Glu Arg Arg Lys Arg Phe
1               5                   10                  15

<210> SEQ ID NO 28
<211> LENGTH: 19
<212> TYPE: PRT
<213> ORGANISM: Homo sapiens

<400> SEQUENCE: 28

Ala Ser Lys Thr Lys Thr Lys Lys His Phe Val Ala Gln Lys Val
1               5                   10                  15

Lys Leu Phe

<210> SEQ ID NO 29
<211> LENGTH: 19
<212> TYPE: PRT
<213> ORGANISM: Homo sapiens

<400> SEQUENCE: 29

Glu Met His Asn Ile Leu Lys Lys Tyr His Gln Tyr Ile Val Glu Cys
1               5                   10                  15

His Gly Ile

<210> SEQ ID NO 30
```

```
<211> LENGTH: 16
<212> TYPE: PRT
<213> ORGANISM: Homo sapiens

<400> SEQUENCE: 30

Ala Lys Lys Lys Ala Ala His Ala Ala Lys Thr Val Lys His Gly Ala
1               5                   10                  15

<210> SEQ ID NO 31
<211> LENGTH: 25
<212> TYPE: PRT
<213> ORGANISM: Homo sapiens

<400> SEQUENCE: 31

Val Lys His Arg Lys Gln Gln Val Leu Glu Thr Val Ala Gly Lys Arg
1               5                   10                  15

Ser Tyr Arg Leu Ser Met Lys Val Lys
            20                  25

<210> SEQ ID NO 32
<211> LENGTH: 14
<212> TYPE: PRT
<213> ORGANISM: Homo sapiens

<400> SEQUENCE: 32

Glu Lys Tyr Lys Ala Lys Ser Arg Ser Pro Gly Ser Pro Val
1               5                   10

<210> SEQ ID NO 33
<211> LENGTH: 9
<212> TYPE: PRT
<213> ORGANISM: Homo sapiens

<400> SEQUENCE: 33

Leu Arg Glu Lys Ser Lys Lys Tyr Ser
1               5

<210> SEQ ID NO 34
<211> LENGTH: 11
<212> TYPE: PRT
<213> ORGANISM: Homo sapiens

<400> SEQUENCE: 34

Leu Arg Glu Lys Ser Lys Lys Tyr Ser Asp Val
1               5                   10

<210> SEQ ID NO 35
<211> LENGTH: 11
<212> TYPE: PRT
<213> ORGANISM: Homo sapiens

<400> SEQUENCE: 35

Glu Arg Lys Gln Lys Gly Ser Glu Glu Asn Leu
1               5                   10

<210> SEQ ID NO 36
<211> LENGTH: 6
<212> TYPE: PRT
<213> ORGANISM: Homo sapiens

<400> SEQUENCE: 36

Glu Arg Lys Gln Lys Gly
1               5
```

<210> SEQ ID NO 37
<211> LENGTH: 27
<212> TYPE: PRT
<213> ORGANISM: Homo sapiens

<400> SEQUENCE: 37

Pro Gly Lys Ser Pro Ser Lys Lys Lys Lys Phe Arg Thr Pro Ser
1               5                   10                  15

Phe Leu Lys Lys Ser Lys Lys Lys Ser Asp Ser
            20                  25

<210> SEQ ID NO 38
<211> LENGTH: 23
<212> TYPE: PRT
<213> ORGANISM: Homo sapiens

<400> SEQUENCE: 38

Gly Lys Ser Pro Ser Lys Lys Lys Lys Phe Arg Thr Pro Ser Phe
1               5                   10                  15

Leu Lys Lys Ser Lys Lys Lys
            20

<210> SEQ ID NO 39
<211> LENGTH: 19
<212> TYPE: PRT
<213> ORGANISM: Homo sapiens

<400> SEQUENCE: 39

Val Ser Lys Lys Glu Tyr Glu Glu Asp Gly Ala Arg Ser Ile His Arg
1               5                   10                  15

Lys Thr Phe

<210> SEQ ID NO 40
<211> LENGTH: 22
<212> TYPE: PRT
<213> ORGANISM: Homo sapiens

<400> SEQUENCE: 40

Met Tyr Arg Arg Lys Ser Lys Gln Ala Leu Arg Asp Tyr Lys Lys Val
1               5                   10                  15

Gln Ile Gln Leu Glu Asn
            20

<210> SEQ ID NO 41
<211> LENGTH: 52
<212> TYPE: PRT
<213> ORGANISM: Homo sapiens

<400> SEQUENCE: 41

Pro Lys Lys Leu Ser Gly Lys Ser Lys Ser Gly Arg Ser Leu Asn Glu
1               5                   10                  15

Glu Leu Gly Asp Glu Asp Ser Glu Lys Lys Arg Lys Gly Ala Phe Phe
            20                  25                  30

Ser Trp Ser Arg Thr Arg Ser Thr Gly Arg Ser Gln Lys Lys Arg Glu
            35                  40                  45

His Gly Asp His
        50

<210> SEQ ID NO 42
<211> LENGTH: 37
<212> TYPE: PRT
<213> ORGANISM: Homo sapiens

<400> SEQUENCE: 42

Asn Ser Ile Lys Ile Lys Gly Glu Asn Gly Asn Ala Arg Asp Pro
1               5                   10                  15

Arg Leu Ser Lys Arg Glu Glu Ser Ile Ala Lys Ile Gly Lys Lys
            20                  25                  30

Tyr Gln Lys Ile Asn
            35

<210> SEQ ID NO 43
<211> LENGTH: 23
<212> TYPE: PRT
<213> ORGANISM: Homo sapiens

<400> SEQUENCE: 43

Glu Lys Lys Asp Gly Asp Lys Lys Lys Lys Ile Lys Glu Lys
1               5                   10                  15

Tyr Ile Asp Gln Glu Glu Leu
            20

<210> SEQ ID NO 44
<211> LENGTH: 16
<212> TYPE: PRT
<213> ORGANISM: Homo sapiens

<400> SEQUENCE: 44

Val Gln Gly Lys Thr Lys Arg Pro Val Asp Leu Lys Ile Lys Asn Leu
1               5                   10                  15

<210> SEQ ID NO 45
<211> LENGTH: 14
<212> TYPE: PRT
<213> ORGANISM: Homo sapiens

<400> SEQUENCE: 45

Val Ser Arg Leu Val Lys Lys Ile Pro Lys Lys Pro Pro Ala
1               5                   10

<210> SEQ ID NO 46
<211> LENGTH: 15
<212> TYPE: PRT
<213> ORGANISM: Homo sapiens

<400> SEQUENCE: 46

Trp Cys Lys Arg Gly Arg Lys Gln Cys Lys Thr His Pro His Phe
1               5                   10                  15

<210> SEQ ID NO 47
<211> LENGTH: 16
<212> TYPE: PRT
<213> ORGANISM: Homo sapiens

<400> SEQUENCE: 47

Phe Gln Lys Ala Lys Glu Arg Leu Glu Ala Lys His Arg Glu Arg Met
1               5                   10                  15

<210> SEQ ID NO 48
<211> LENGTH: 23
<212> TYPE: PRT
<213> ORGANISM: Homo sapiens

<400> SEQUENCE: 48

Leu Arg Lys Asn Lys Asn Ile Asp Asn Phe Leu Asn Arg Tyr Glu Lys

```
                1               5                  10                 15

Ile Val Lys Lys Ile Arg Gly
            20

<210> SEQ ID NO 49
<211> LENGTH: 8
<212> TYPE: PRT
<213> ORGANISM: Homo sapiens

<400> SEQUENCE: 49

Glu Lys Lys Lys Lys Ile Thr Val
1               5

<210> SEQ ID NO 50
<211> LENGTH: 16
<212> TYPE: PRT
<213> ORGANISM: Homo sapiens

<400> SEQUENCE: 50

Asn Arg Lys Lys His Arg Arg Lys Lys Ser Thr Ser Asn Phe Lys Ala
1               5                   10                  15

<210> SEQ ID NO 51
<211> LENGTH: 11
<212> TYPE: PRT
<213> ORGANISM: Homo sapiens

<400> SEQUENCE: 51

Phe Arg Gly Arg His Tyr Lys Arg Glu Phe Arg
1               5                   10

<210> SEQ ID NO 52
<211> LENGTH: 8
<212> TYPE: PRT
<213> ORGANISM: Homo sapiens

<400> SEQUENCE: 52

Leu Arg Ile Lys Lys Lys Lys Glu
1               5

<210> SEQ ID NO 53
<211> LENGTH: 11
<212> TYPE: PRT
<213> ORGANISM: Homo sapiens

<400> SEQUENCE: 53

His Arg Arg Cys Lys His Arg Thr Gly Lys Ala
1               5                   10

<210> SEQ ID NO 54
<211> LENGTH: 11
<212> TYPE: PRT
<213> ORGANISM: Homo sapiens

<400> SEQUENCE: 54

Phe Arg Gly Arg His Tyr Lys Arg Glu Phe Arg
1               5                   10

<210> SEQ ID NO 55
<211> LENGTH: 16
<212> TYPE: PRT
<213> ORGANISM: Homo sapiens

<400> SEQUENCE: 55
```

```
Phe Lys Lys Glu Lys Asn Asn Lys Asn Lys Glu Ala His Ser Ser Leu
1               5                   10                  15
```

<210> SEQ ID NO 56
<211> LENGTH: 6
<212> TYPE: PRT
<213> ORGANISM: Homo sapiens

<400> SEQUENCE: 56

```
Phe Lys Lys Glu Lys Asn
1               5
```

<210> SEQ ID NO 57
<211> LENGTH: 11
<212> TYPE: PRT
<213> ORGANISM: Homo sapiens

<400> SEQUENCE: 57

```
Ala Arg Glu Gly Lys Asp Ser Lys Glu Lys Leu
1               5                   10
```

<210> SEQ ID NO 58
<211> LENGTH: 28
<212> TYPE: PRT
<213> ORGANISM: Homo sapiens

<400> SEQUENCE: 58

```
Pro Arg Lys Gly Pro Pro Lys Phe Lys Gln Arg Gln Thr Arg Gln Phe
1               5                   10                  15

Lys Ser Lys Pro Pro Lys Lys Gly Val Lys Gly Phe
            20                  25
```

MODIFICATION OF INTRINSICALLY DISORDERED SEQUENCES FOR THE PREPARATION OF VACCINES

FIELD OF THE INVENTION

The goal of the present invention is the induction of an immune reaction removing the pathology caused by modifications of cellular physiology due to the aggregation of intrinsically disordered sequences (IDSeq). The invention describes the use of the intrinsically disordered sequences in which a secondary group, of one or more amino acids reacted with a small molecule able to carry out a polymerization with another IDSeq. Polymers of the covalently modified IDSeq are used in vivo to induce an immunological response, in order to stop or prevent a disease. The antibodies obtained by this method are used for the suppression of pathologies associated with a metabolic disorder occurring in infections or metabolic diseases, the diagnosis or studies of the development of such diseases.

BASIS OF THE INVENTION

The patent of H. Malina EP001165600 described a use of the proteins covalently modified by xanthurenic acid for the preparation of vaccine. Xanthurenic acid, a small molecule from the pathway of the oxidative degradation of tryptophan by indoleamine 2,3-dioxygenase, modifies the proteins in a covalent way and mimics the process of covalent modification of proteins in vivo in ageing or infections. The mechanism of development of the diseases was established on the basis of the study of xanthurenic acid in the cell culture of the human and animal cells. The interactome is a controlled protein network, where the interactions between proteins are reversible. The invention is based on previous studies showing that the covalent modifications of proteins in the presence of xanthurenic acid lead to pathological apoptosis (Malina et al. Physiology of BMC 2001).

Pathological apoptosis is caused by misfolded protein networks, and is associated with the attachment of calmoduline (Cam) to the protein sites regulated by the calmoduline. In parallel, the phoshatidylinositol phosphate (PIP2), cannot any further control these sequences bound to calmoduline. The lack of the signalling of calmoduline/PIP2 abolishes the regulation of Bax by the PIP2, and leads to covalent binding of Bax to CAM, and the pathological apoptosis associated with constitutive activation of the caspase-3 due to the activation of the mitochondrial caspase-9 (Malina H, not published). In vivo and in vitro, the polymerization of proteins is produced by small molecules like xanthurenic acid, which can bind covalently to proteins and lead to their polymerization.

These small molecules present in the human body can come from the metabolism, from pollution, but also for example, from endogenous therapy by small molecules. These molecules lead to covalent interactions between proteins. The model molecule to study the formation of <<misfoldome>> in vivo and in vitro is xanthurenic acid, which allows the establishment of the pathologic interactions between proteins leading to development of the diseases, and causing damage of mitochondria (Malina et al. BMC Cell Biology 2004.), a lack of regulation of calcium (Malina et al. BMC Opthalmology 2002), and an interruption of signaling of the proteins 14-3-3 (Malina et al. BBRC 2003).

The modified proteins have new covalent interactions with other proteins, and change their place and their role in the cell. The sequences having a group of three basic amino acids are modified preferentially by the small molecules in a covalent way, and can be used for the preparation of the antibodies and modification of the network of calmoduline and phosphatidylinositol phosphate (Malina H., Patent Fr 0604671). The present invention revealed the method of preparation of the antibodies against polymerized peptides, which correspond to region called IDSeq, which modification is responsible for the development of the diseases.

Many regions of proteins proved to be intrinsically disordered. The intrinsically disordered sequences are crucial for the function of proteins, particularly those involved in signalling and regulation (Chen W. J and Al J. Proteome Res.5, 879-887, 2006). The identification of the region of proteins is very important for the forecast of their structure and their functional characterization. The regions of the protein, unstructured intrinsically, play a key role in the signalling of the cells, the degeneration of the cells, and cancer (Jakoucheva L M, brown C J, Lawson J D, Obradowicz Z, Dunker A K, J. Mol. Biol. 323,573-584, 2002). The "unfoldability" of the sequences is caused by the high charge of these sequences rich in lysine, arginine, histidine and glutamine present in IDSeq. IDSeq of proteins are detected for example by the FoldIndex© software (Jaime Prilusky, Tzviya Zeev-Ben-Mordehai, Edwin Rydberg, Clifford Felder, Israel Silman and Joel L. Sussman, based on the algorithm proposed by Uversky V N, Gillespie J R, and Fink A L. Why are "natively unfolded" proteins unstructured under physiologic conditions? Proteins 2000; 41:415-427.)

The invention is based on the discovery showing that apoptosis in ageing and infections, called pathological apoptosis, is caused by the covalently modified proteins. The covalently modified proteins change localization in the cell because of the new covalent interactions between proteins. On the contrary, the physiological state is ensured by the network of the electrostatically bound proteins, the interactome. Interactions between proteins in the interactome are flexible in order to ensure the regulation of proteins. Flexibility is ensured by the regions of protein responsible for its regulation, and called the intrinsically disordered sequences. The pathology of the cells is caused by these sequences (IDSeq), which are covalently modified, and cannot take part any more in the regulation. This invention reveals a new technology of preparation of vaccines by using these sequences modified and polymerized, which can be employed to detect the early development of the diseases, to prevent them or cure them. Segments of the sequences characterized as intrinsically disordered, defined for example with the aid of FoldIndex©, correspond to the sequences used for the development of drugs in the present invention.

This method revealed the preparation of the vaccines, by using a polymer of the covalently modified IDSeq, called the pIDSeqC. The pIDSeqC's cannot play a regulatory role, and induce elsewhere a new and strong signalling, overwriting the normal signalling from the interactome. The new covalent interactions between proteins lead to the pathology of the cells and the metabolic disorders associated with ageing or the infections.

The therapy or the prevention of the diseases according to this invention is made by the elimination of pIDSeqC, because "unfoldability" is necessary for a normal physiological state of mammals. A passive or active vaccination by pIDSeqC elimines a pathology caused by these covalent interactions. The invention differs from current therapy, which targets the normal proteins or peptides. The invention permits further therapeutic possibilities by the induction of an immunological response against the covalent interactions between IDseqCs.

DESCRIPTION OF THE INVENTION

Various terms connected to the methods and other aspects of this invention are used in the specifications and the claims.

The term "small polymerizing molecules" holds for any molecule able to react with a secondary group of amino acids, and leading to the polymerization from one, two or several peptides.

The term "misfolded proteins" means that the proteins were covalently modified, in a way that a small molecule, a lipid or a regulaory protein cannot have electrostatic interaction with this sequence.

Covalent modification of IDSeq means that the charged amino-acids are modified so that they become nonaccessible, and this in a final way, for a small molecule or for an electrostatic regulation by protein.

The polymerization of IDSeqC means that IDSeqC, belonging to the same or various proteins, form a dimer or a polymer. The covalent modification of peptides can have as consequence aggregation of peptides, where one or more peptides and one or more small molecules are used for the preparation of the aggregate.

The terms "polymerized proteins", aggregated proteins" and "crosslinked proteins" are used below interchangeably.

Vaccination or immunization against misfolded proteins consists of the introduction of the sequences pIDSeqC into a living organism, by any known means as for example: a sublingual, nasal, dermic application or an injection in a living organism of an antibody obtained by the use of pIDSeqC-like antigen.

The therapy represents any success of improvement of the physical or mental wellbeing of human, by the attenuation of any degenerative process induced by infection, trauma or ageing, including, without limitation, but for example: ageing of the skin, anxiety, depression, blood circulation, reduction in vision, neurological degeneration, diseases of the heart, hepatic affections, osteoporosis, immunosuppression or cancers.

"Medium pharmaceutically acceptable" refers to a medium which does not interfere with the effectiveness of biological activity of the active ingredients, and is not toxic for the organism to which it is administrated.

"Predicted disorder segment" is a fragment of a sequence, which must remain accessible for a regulation and in the case of the covalent modification leads to disease. Antibodies against these modified sequences are used for therapy.

IDSeq mentioned in the present invention means that a peptide is determined, by the software of FoldIndex©, to be like an intrinsically disordered segment. Immunization refers to induction of immunity in the animal or human, by any accessible means, by using the IDSeqC polymer.

Vaccination targets the pathology caused by the polymerized sequences. Many diseases are associated with the degeneration of the tissue, which is caused by pathological apoptosis. Pathological apoptosis is caused by the covalent interactions between proteins. In contradistinction, apoptosis observed in tissue homeostasis and in development, is caused by physiological interactions. According to this invention, the therapy for the diseases is possible by immune reaction against the pIDSeqC of proteins. These modified proteins can be the membrane proteins (especially G-proteins and GPRC), the cytoplasmic proteins or nuclear proteins (for example receptor RAR etc). Modification covalent of proteins, like the protein precursor of the prion, the protein precursor of beta-amyloide, CD19, EGFR, VEGFR, the proteins suppressors of tumours as for example the protein of regulation of the suppressor of the glioma tumour, the protein p53, proteins RGS, receptors of chemokines, and interleukins, led to their aggregation (polymerization) which exerts a new signaling which is pathological. The proteins are polymerized by small molecules (for example: endogenous xanthurenic acid or drugs like Endoxan, the small molecules of pollution or cigarette smoke), which modify in an irreversible, covalent way the secondary amine groups of amino acids.

An important mechanism leading to the diseases, is the reduction of the production of the PIP2, due to the polymerization of IDSeqC in the membranes, leading to loss of activity of PI-4 kinase and PI-5 kinase, and a covalent polymerization of IDSeqC of the PI3 kinase p85 and p100. Interaction of IDSeqC of these kinases with the binding sites of phosphatidylinositol phosphates of proteins, like gelsolin, PLC, EGFR, adducin etc makes impossible the regulation of these proteins by PIP2. In the same manner, the polymerization of IDSeqC of proteins controlled by the PIP2, with a sequence of G-proteins or any protein associated with the G-protein network, eliminates physiological signalling, and causes the diseases. The platform of technology for the preparation of the drugs, according to this invention, consists to choose, by the FoldIndex software, one or more IDSeq of a protein suspected to be involved in a disease. The antigen prepared by the polymerization of the peptides is injected into a living organism for induction of the immune response. The therapeutic efficacy of the antibody present in the serum of the animal, can be estimated without further purification, by using it in a cell culture in the presence of xanthurenic acid. The antibody purification can be performed by any method for antibody purification, and improved by any technological method. For example, the antibody polyclonal purified by affinity chromatography is an effective, passive therapeutic vaccine, because corresponds to situation in vivo of the formation des proteins leading to diseases.

DETAILED DESCRIPTION

The electrostatic interactions between proteins in the membranes, and in particular in the "lipid rafts", are responsible for the regulation of signalling in the cells. One of the events upstream of cellular pathology, are the covalent interactions of proteins involved in the network of proteins, the interactions of GPCR, the synthesis of phospholipides phosphates, 14-3-3 proteins, proteins controlled by the calmoduline, as well as proteins of the membranes, like beta-amyloide protein precursor protein, precursor of prion protein, PAR, adducin, of the regulatory proteins of the cancer genes suppressors, the receptor for chemokines, interleukines, neuregulin, EGFR, VGFR, TGFR, etc. The invention describes a technology of preparation of the drugs by using the peptides modified in a covalent way. The peptide is synthesized in vitro, and its secondary amino groups are left free for modification. A peptide or peptides can be modified by any method, but an incubation, with a solution of the polymerizing substance, is a satisfactory method. The time and the condition of the modification depend on the degree of modification to be attained. The polymerizing substance is added to peptide, preferably in a molar ratio corresponding to the number of the amino acids to modify in the peptide. The pIDSeqC are employed like antigen, to induce an immune reaction. The presence of a phosphoryl group as the peptide modification, changes the characteristics of the antibody that is produced.

The generation of antibodies against a polymerizated protein is identical to the situation during the development of the diseases associated with ageing or infections. The antibodies against the pIDSeqC have therapeutic activities in vitro and in vivo, and stop pathology in the human and the animal. These misfolded peptides are used for the vaccination of mammals, preferably an animal. The human is preferably treated by antibody obtained against the IDSeqC in an animal, to avoid an uncontrolled production of the antibody in the human. However, certain antigens, and in certain particular clinical situations, can be employed directly in human-like vaccine.

The antibody can act directly on the cells to block the misfolded proteins in the cell membrane and to prevent pathology, and, for example, lead to protection against pathological apoptosis in cell culture or a wound. The antibody can be a polyclonal antibody, a single chain antibody, a recombinant antibody or an antibody prepared by any existing or future synthetic process leading to the production of the antibody's active constituents. The antibodies prepared on this platform block in vivo the networks of the covalently modified proteins and in the same manner the antibody will remove the signalling of the incorrect interactions leading to the diseases. Xanthurenic acid is a model substance, very convenient for the polymerization of peptides, because is soluble in water, has yellow colour, and is flourescent. The attachment covalent of the xanthurenic acid—or any derivative of the xanthurenic acid—to peptides, mimic the situation of the modification in vivo. This approach leads to the preparation of effective antibodies against misfolded peptides, which remove pathology in vivo. Thin layer chromatography and mass spectrometry can be used to monitor the modification of the peptide. The antibody against the pIDSeqC is produced in an animal, preferably by three injections made to the animal at intervals of one months to six weeks. The serum of the animal has a therapeutic activity, and leads to suppression of the pathology of the cells in a primary cell culture, in humans and animals. For a higher biological activity, the serum is purified by affinity chromatography on any accessible chromatographic support. The antibodies against the pIDSeqC have a therapeutic activity in vitro and in vivo, and stop pathology in human and animals. The antibody can be delivered in any known manner, preferably by application or injection for therapy of human, and by injection for animal therapy. The antibodies can act by blocking the misfolded proteins in the cell membrane, leading to protection against pathologies. The examples below show the preparation of the vaccines by using IDSeqC.

It is claimed a use of modified sequences of proteins for the manufacture of cosmetics, and for the diagnosis and treatment of diseases.

Example 1

An incubation of a peptide, having IDSeq, with xanthurenic acid, led to the covalent modification of this peptide and its dimerisation (pIDSeqC) observed by MS. The product of the reaction, named pIDSeqC, was used as an antigen. 1 ml containing 400 micrograms of the modified peptide in 1 ml 7.2 phosphate buffer was mixed with 1 ml of Freund's adjuvant. The rabbits were injected three times, once every six weeks. The rabbits produced the desired antibody, thus against the sequence modified by the xanthurenic acid, as it was shown by the Western blot analysis, because the antibody recognized the sequence in a protein sample which was cultivated in the presence of the xanthurenic acid, but not in a control culture. A standard protocol was used for the preparation of plasma, and the antibody was purified from plasma by Sepharose conjugated with G-proteins, immunoprecipitation by an anti-pIDSeqC antibody, and their analysis by Western blots were used for studies of the cell pathology. The antibodies introduced into a cellular culture blocked the pathological interactions caused by the xanthurenic acid. The antibodies showed an accumulation of the modified sequences in blood allowing early diagnosis of diseases caused by the modification of these sequences from the blood. A passive immunization in vivo (human and animal), led to the elimination of these modified sequences, and a suppression of pathologies induced by the wrong signalling of these proteins.

Example 2

130 kDa phosphatidylinositol 4,5-biphosphate-dependent ARF1 GTPase-activating protein (Q9ULH1) The sequence of this protein, named below sequence 1, was synthesized and modified as described in Example 1. La séquence 1:

```
                                          (SEQ ID NO: 1)
  320-N KEYGSEKKGY LLKKSDGIRK VWQRRKCSVK N-351
```

Predicted disorder segment: [1]-[32] length: 32 score: −0.47±0.00

Antibodies against the sequence established the synthesis of PIP2 in the cell.

Example 3

B-lymphocyte antigen CD19 (P15391)
Sequence 2:

```
316 LVLR RKRKRMTDPTRRFFKV 335     (SEQ ID NO: 2)
```

Predicted disorder segment: [1]-[20] length: 20 score: −0.71±0.00

Antibody against the sequence 2-pIDSeqC, prepared as described in Example 1 prevents the accumulation of lymphocytes having this sequence in blood.

Example 4

130 kDa phosphatidylinositol 4,5-biphosphate-dependent ARF1 GTPase-activating protein (Q9ULH1).
Sequence 3:

```
                                          (SEQ ID NO: 3)
    NKEYGSEKKG YLLKKSDGIR KVWQRRKCSV KNGIL
```

Predicted disorder segment: [1]-[35] length: 35 score: −0.42±0.08

Antibodies against the sequence 3-pIDSeqC, were prepared as described in Example 1.

Antibodies prevented the pathological apoptosis.

Example 5

ROCK2_HUMAN Rho-associated protein kinase 2 (O75116)
Sequences 4 et 5.

1165    TKKFGWVKKY V    1175    (SEQ ID NO: 4)

Predicted disorder segment: [1]-[11] length: 11 score: −0.27±0.12

1344    VKKIPKKP    1352    (SEQ ID NO: 5)

Predicted disorder segment: [1]-[8] length: 8 score: −0.79±0.29

Antibodies against sequences 4 and 5-pIDSeqC, were prepared as described in Example 1.
Antibodies prevented modification of ROCK2.

Example 6

Phosphatidylinositol-3,4,5-trisphosphate 3-phosphatase and dual-specificity protein phosphatase PTEN(Q6XPS3)
Sequences 6 et 7.

257    FHKQNKMLKK DKMFHF    271    (SEQ ID NO: 6)

Predicted disorder segment: [1]-[16] length: 16 score: −0.57±0.27

158    RDIYETDYYRKGGK    171    (SEQ ID NO: 7)

Predicted disorder segment: [1]-[14] length: 14 score: −0.66±0.18

Antibodies against the sequences 5-pIDSeqC, were prepared as described in Example 1.
Antibodies prevented PTEN anormality.

Example 7

EGFR récepteur (P00533)
Sequence 8: (SEQ ID NO: 8)

```
216 NCQKLTKIIC AQQCSGRCRG KSPSDCCHNQ CAAGCTGPRE SDCLVCRKFR
251 DEATCKDTCP PLMLYNPTTY QMDVNPEGKY SFGATCVKKC PRN          299
```

Predicted disorder segment: [1]-[5] length: 5 score: −0.29±0.09
Predicted disorder segment: [14]-[27] length: 14 score: −0.40±0.26
Predicted disorder segment: [36]-[41] length: 6 score: −0.36±0.20
Predicted disorder segment: [47]-[54] length: 8 score: −0.43±0.19
Predicted disorder segment: [67]-[81] length: 15 score: −0.25±0.15
Predicted disorder segment: [86]-[93] length: 8 score: −0.38±0.43

Antibodies against the sequences 8-pIDSeqC, were prepared as described in Example 1.
Antibodies prevented the abnormal signaling of the modified receptor.

Example 8

Pro-neuregulin-1 (Q02297)
(Glial growth factor) observed in breast cancer.
Séquence 9:

(SEQ ID NO: 9)
0    MSERKEGRGK GKGKKKERGS GKKPESA    27

Antibodies against the sequence 9-pIDSeqC, were prepared as described in Example 1.
Antibodies prevented the nucleus anormalities.

Example 9

14-3-3 protein gamma (P61981)
Séquence 10:

75    EKKIE MVRAYREKIE KELEAV    96    (SEQ ID NO: 10)

Predicted disorder segment: [1]-[8] length: 8 score: −0.28±0.15
Antibodies against the sequence 10-pIDSeqC, were prepared as described in Example 1.
Antibodies prevented the pathological apoptosis.

Example 10

Actin-depolymerizing factor (P06396)
Sequence 11:

161    FKSGLKYKKG    170    (SEQ ID NO: 11)

Predicted disorder segment: [1]-[10] length: 10 score: −0.53±0.00
Antibodies against the sequence 11-pIDSeqC, were prepared as described in Example 1.
Antibodies prevented the pathological apoptosis.

Example 11

Phosphatidylinositol-3, 4, 5-trisphosphate 3-phosphatase TPTE2 Synonyms EC 3.1.3.67, TPTE and PTEN homologous inositol lipid phosphatase
Séquences 12

250    VRFLDKKHRN HYRVYNLCSE RA    271    (SEQ ID N° 12)

Predicted disorder segment: [1]-[14] length: 14 score: −0.64±0.28

```
 1 NCQKLTKIIC AQQCSGRCRG KSPSDCCHNQ CAAGCTGPRE SDCLVCRKFR
51 DEATCKDTCP PLMLYNPTTY QMDVNPEGKY SFGATCVKKC PRNRKCKKCEGPC RKV
```

Antibodies against the sequence 12 pIDSeqC, were prepared as described in example 1.
Antibodies prevented the modification of TPTE2

Example 12

Rho/Rac guanine nucleotide exchange factor 2 (P05067)
Sequences 13:

```
WCKRGRKQCK THPHF      195     (SEQ ID N° 13)
```

Predicted disorder segment: [1]-[15] length: 15 score: −0.64±0.00

```
FQKAKERLEA KHRERMSQVM REW  440   (SEQ ID N° 14)
```

Predicted disorder segment: [1]-[23] length: 23 score: −0.46±0.14
Antibodies against sequences 13 and 14 pDSeqC, were prepared as described in Example 1.
Antibodies prevented the pathological apoptosis.

Example 13

Amyloid beta A4 precursor protein-binding family B member 1-interacting protein (Q7Z5R6) Sequence 15:

```
159  AKA DKIKLALEKL KEAKVKKLV 180   (SEQ ID NO: 15)
```

Antibodies against the sequences 15 pDSeqC, were prepared as described in Example 1.
Antibodies prevented the pathological apoptosis and beta-amyloid aggregation.

Example 14

Brain-specific angiogenesis inhibitor 1-associated protein 2 BAIP2 HUMAN (Q9UQB8)
Insulin receptor substrate p53
Sequence 16:
Predicted disorder segment: [1]-[43] length: 43 score: −0.48±0.23

```
                                       (SEQ ID NO: 16)
ALKKYQTEQR SKGDALDKCQ AELKKLRKKS QGSKNPQKYS DKE
```

Antibodies against the sequence 16 pIDSeqC, were prepared as described in Example 1.
Antibodies prevented the pathological apoptosis and the modification of insulin receptor.

Example 15

HUMAN Q59GZ4
La séquence 17:
Molecular function: protein serine/threonine kinase activity

```
NRKDFKIDRK KA         (SEQ ID NO: 17)
```

Predicted disorder segment: [1]-[12] length: 12 score: −0.77±0.15
Antibodies against the sequence 17 pIDSeqC, were prepared as described in Example 1.
Antibodies prevented the pathological apoptosis and kinase modification.

Example 16

Rho family, small GTP binding protein Rac1 (P 63000)
Séquence 18:

```
181    P VKKRKRKCL     190    (SEQ ID N: 18)
```

Antibodies against the sequence 18 pIDSeqC, were prepared as described in Example 1.
Antibodies prevented the pathological apoptosis.

Example 17

Breast cancer nuclear receptor-binding auxiliary protein (Q 12802).
Sequences 19, 20, 21:

```
                                       (SEQ ID NO: 19)
TRLFGLTKPK EKKEKKKKNK TSRSQPGDGP A    2801

(SEQ ID NO: 20)
FS YIKNKMSSSK KSKEKEKEKD KIKEKEKDSK   1794
DKEKDKKTVN GHTF (SEQ ID NO: 21)
NTDRSCR KKNKGVERKG E                   381
```

Antibodies against the sequences 19,20,21 pIDSeqC, were prepared as described in Example 1. Antibodies prevented anormality of nucleus.

Example 18

A-Raf proto-oncogene serine/threonine-protein kinase Synonyms EC 2.7.11.1
Sequences 22:

```
                                       (SEQ ID NO: 22)
261  ASVSSGRKSP HSKSPAEQRE RKSLADDKKK VKNLGYRD 297
```

Predicted disorder segment: [1]-[38] length: 38 score: −0.52±0.17
Antibodies against the sequence 22 pIDSeqC, were prepared as described in Example 1.
Antibodies prevented anormality of kinase.

Example 19

AB1 kinase
Sequences 23 et 24:

```
1    EESRVRRHKH SSESPGRDKG    (SEQ ID NO: 23)
```

Predicted disorder segment: [1]-[20] length: 20 score: −0.67±0.26
FLRRKRD (SEQ ID NO: 24)
Predicted disorder segment: [1]-[7] length: 7 score: −0.67±0.41
Antibodies against the sequences 23 and 24 pIDSeqC, were prepared as described in Example 1. Antibodies prevented anormality of nucleus.

Example 20

Tubby protein (P 50607)

Sequence 25:

```
122    ARKEKKGK HKG    132    (SEQ ID NO: 25)
```

Antibodies against the sequences 25 pIDSeqC, were prepared as described in Example 1.

Antibodies prevented anormality of the cytoskeleton.

Example 21

Myosin phosphatase Rho-interacting protein (Q6WCQ1).

La séquence 26 et 27:

```
152    NKQNQKKKRK V    162    (SEQ ID NO: 26)
```

Predicted disorder segment: [1]-[11] length: 11 score: −1.48±0.21

```
581    ERERARRREE RRKRF    585    (SEQ ID NO: 27)
```

Predicted disorder segment: [1]-[15] length: 15 score: −1.23±0.19

Antibodies against sequences 26 and 27 pIDSeqC, were prepared as described in Example 1.

Antibodies prevented the apoptose pathological and established phosphorylation of the myosine.

Example 22

PtdIns(5)P-4-kinase isoform 2-alpha (P 48426).

Sequences 28, 29, 30:

```
18    ASKTKTKKKH FVAQKVKLF    31    (SEQ ID NO: 28)

153   EMHNILK KYHQYIVECH GI    172   (SEQ ID NO: 29)

365   AKKKA AHAAKTVKHG A    381    (SEQ ID NO: 30)
```

Antibodies against sequence 28, 29 and 30 pIDSeqC, were prepared as described in Example 1. Antibodies prevented the pathological apoptosis.

Example 23

VGFR 1 (P17948)

Les séquences 31:

```
                                          (SEQ ID NO: 31)
345    VKHRK QQVLETVAGK RSYRLSMKVK    360
```

Antibodies against the sequence 31 pIDSeqC, were prepared as described in Example 1.

Antibodies prevented formation of the new vessels.

Example 24

Alpha-Adducin (P 35611)

Les séquences 32, 33, 34, 35, 36, 37, 38:

```
                                          (SEQ ID NO: 32)
EKYK AKSRSPGSPV                                      360
```

EKYKAKSRSPGSPV 14 residues, unfoldability −0.437 (Charge: 0.214, Phobic: 0.333)

```
                                          (SEQ ID NO: 33)
REKSKKYS 8 residues, unfoldability −1.008
(Charge: 0.375, Phobic: 0.186)
```

```
                                          (SEQ ID NO: 34)
L REKSKKYSDV                                         410
```

```
                                          (SEQ ID NO: 35)
E RKQKGSEENL                                         590
```

```
                                          (SEQ ID NO: 36)
ERKQKG 6 residues, unfoldability −1.108 (Charge:
0.333, Phobic: 0.135)
```

```
                                          (SEQ ID NO: 37)
PGKSPSKKKK KFRTPSFLKK SKKKSDS                        730
```

```
                                          (SEQ ID NO: 38)
GKSPSKKKKKFRTPSFLKKSKKK 23 residues, unfold-
ability −0.892 (Charge: 0.522, Phobic: 0.280)
```

Antibodies against the sequences 32, 33, 34, 35, 36, 37, 38 pIDSeqC, were prepared as described in Example 1. Antibodies prevented degeneration of cytoskeleton in a cellular culture.

Example 25

Centrosome-associated actin homolog (P61163)

Sequences 39 et 40:

```
VSKKEYEEDG ARSIHRKTF    376    (SEQ ID NO: 39)
```

Predicted disorder segment: [1]-[19] length: 19 score: −0.28±0.00

```
MYRRKSKQAL RDYKKVQIQL EN    (SEQ ID NO: 40)
```

Predicted disorder segment: [1]-[22] length: 22 score: −0.46±0.00

Antibodies against sequences 39 and 40 pIDSeqC, were prepared as described in Example 1.

Antibodies prevented formation the cells with multiple nuclei.

Example 26

Regulator of G-protein signalling 12 (A2A496)
Les séquences 41 et 42:

(SEQ ID NO: 41)
219 PKKLSGKSKSGRSLNEELGDEDSEKKRKGAFFSWSRTRSTGRSQKKREHGDH A 271

Predicted disorder segment: [1]-[53] length: 53 score: −0.54±0.23

(SEQ ID NO: 42)
499 NS IKIKGENGKN ARDPRLSKRE ESIAKIGKKK YQKIN 535

Predicted disorder segment: [1]-[37] length: 37 score: −0.44±0.15

Antibodies against the sequences 41 and 42 pIDSeqC, were prepared as described in Example 1. Antibodies prevented the pathological apoptosis.

Example 27

Heat shock protein HSP 90-alpha (P07900).
Sequences 43:

267 EKK DGDKKKKKI KEKYIDQEEL-290 (SEQ ID NO: 43)

Antibodies against the sequence 43 pIDSeqC, were prepared as described in Example 1.
Antibodies abolished the anormality of nucleus.

Example 28

T-cell activation Rho GTPase-activating protein (Q8N103)
Les séquences 44 et 45 a, b:

VQGKTKRPVD LKIKNL    (SEQ ID NO: 44)

Predicted disorder segment: [1]-[14] length: 14 score: −0.45±0.15

VSRLVKKIPK KPPA    (SEQ ID NO: 45)

Predicted disorder segment: [5]-[14] length: 10 score: −0.53±0.22

Antibodies against sequences 44 and 45 pIDSeqC, were prepared as described in Example 1.
Antibodies prevented the pathological apoptosis.

Example 29

Rho/Rac guanine nucleotide exchange factor 2 (Q92974).
Sequences 46 et 47:

WCKRGRKQCK THPHF 200    (SEQ ID NO: 46)

Predicted disorder segment: [1]-[23] length: 23 score: −0.46±0.14

FQKAKERLEA KHRERM 433    (SEQ ID NO: 47)

Predicted disorder segment: [1]-[16] length: 16 score: −0.56±0.30

Antibodies against sequences 46 and 47 pIDSeqC, were prepared as described in Example 1.

Antibodies prevented the pathological apoptosis.

Example 30

Rho kinase 2 (O 507516).
Sequence 48.

62 LRKNKNIDNF LNRYEKIVKK IRG 85    (SEQ ID N° 29)

Predicted disorder segment: [1]-[7] length: 7 score: −0.66±0.39

Antibodies against the sequence 48 pIDSeqC, were prepared as described in Example 1.
Antibodies prevented the pathological apoptosis.

Example 31

RAR
Retinal-specific ATP-binding cassette transporter.
La séquence 49:

350 EKKKKITV 363    (SEQ ID NO: 49)

Predicted disorder segment: [1]-[5] length: 5 score: −0.54±0.00

Antibodies against the sequence 49 pIDSeqC, were prepared as described in Example 1.
Antibodies abolished the anormality of nucleus.

Example 32

ARF-GAP with GTP-binding protein-like, ankyrin repeat and pleckstrin homology domains 1 (Q9UPQ3).
La séquence 50:

524 NRKKHR RKKSTSNFKA 540    (SEQ ID NO: 50)

Predicted disorder segment: [1]-[16] length: 16 score: −1.12±0.21

Antibodies against sequence 50 pIDSeqC, were prepared as described in Example 1.
Antibodies prevented the pathological apoptosis.

Example 33

Receptor interleukin 1 beta (P01584)
Les séquence 51, 52, 53 a, b, c:

F RGRHYKREFR 40    (SEQ ID NO: 51)

Predicted disorder segment: [1]-[11] length: 11 score: −0.95±0.26

LRIKK KKE 230    (SEQ ID NO: 52)

Predicted disorder segment: [1]-[8] length: 8 score: −1.08±0.29

```
    H RRCKHRTGKA 380        (SEQ ID NO: 53)
```

Predicted disorder segment: [1]-[11] length: 11 score: −0.98±0.29

Antibodies against the sequences 51, 52, 53 pIDSeqC, were prepared as described in Example 1. Antibodies prevented the pathological apoptosis and inflammation.

Example 34

Interleukin 15 receptor Q13261
La séquence 54:

```
    F RGRHYKREFR 70         (SEQ ID NO: 54)
```

Antibodies against the sequence 54 pIDSeqC, were prepared as described in Example 1.
Antibodies prevented the modification of this protein Example 35

Diacylglycerol kinase delta (Q16760) cytoplasm:
La séquence 55 et 56:

```
    1 FKKEKNNKNK EAHSSL     (SEQ ID NO: 55)
```

Predicted disorder segment: [1]-[16] length: 16 score: −0.84±0.27

```
    1 FKKEKN                (SEQ ID NO: 56)
```

Predicted disorder segment: [1]-[6] length: 6 score: −0.91±0.00

Antibodies against sequences 55 and 56 pIDSeqC, were prepared as described in Example 1.
Antibodies prevented the anormality of the kinase.

Example 36

WD repeat domain phosphoinositide-interacting protein 4 (Q9Y484)
Sequence 57

```
    85 AREGKDSKEK L 94      (SEQ ID NO: 57)
```

Predicted disorder segment: [1]-[11] length: 11 score: −0.48±0.00

Antibodies against the sequence 57 pIDSeqC, were prepared as described in Example 1.
Antibodies prevented the pathological apoptosis.

Example 37

Retinal cone rhodopsin-sensitive cGMP 3',5'-cyclic phosphodiesterase subunit gamma Q13956
Sequence 58.

```
19 PRKGPPKFKQ RQTRQFKSKP PKKGVKGF 46 (SEQ ID NO: 58)
```

Predicted disorder segment: [1]-[28] length: 28 score: −0.84±0.14

Antibodies against the sequence 58 pIDSeqC, were prepared as described in Example 1.
Antibodies prevented a degeneration of cells of the retina.

Example 38

La SEQ ID: 11 et la SEQ: ID 18.
Anticorps contre SEQ ID: 11 et SEQ: ID 18.
(peptides mixed together 1 mole: 1 mole) pIDSeqC, were prepared as described in Example 1.
Antibodies prevented a degeneration of cells, inflammation, beta-amyloid aggregation.

In conclusion the invention describes:

A process intended to cause immune reactions by introduction into a living organism, which uses a product containing one or more peptides corresponding to intrinsically disordered sequences, determined by the Foldindex software, which are covalently modified. In the compound the peptides are polymerized. The compound contains peptides belonging to the same protein or to different proteins. The compound contains one or more intrinsically disordered sequences of proteins presented in examples 2 to 37. The compound contains one or part of the protein sequences presented in examples 2 to 37. The compound contains a mixture of the sequences presented in examples 2 to 37. A compound according to this invention is used for the manufacture of a product for diagnosis, cosmetic or drug treatments for the prevention or therapy of degenerative diseases, for activation of the immune system, therapy of cancers, cardiomyopathy, hypertension, stroke, circulation of blood, regulation of blood lipids, atherosclerosis, degeneration of cardiac valves, ophthalmic diseases such as degeneration of the retina, glaucoma, cataract; osteoporosis, and the dysfunctions of the ionic channels, prion diseases, Parkinson's, Alzheimer's, and any other disease associated with accumulation with beta-amyloid such as kidney degeneration.

The invention claimed is:

1. A method of preparing an antibody comprising introduction into a non-human living organism of an antigen consisting of one peptide which is covalently and irreversibly cross-linked to itself or to a different peptide with xanthurenic acid, wherein said cross-linking occurs at one or more secondary amine groups, and wherein each said peptide is selected from any one of the intrinsically disordered sequences of SEQ ID NO: 1 to 58, such that an antibody is isolated from the organism.

2. The method according to claim 1 in which at least one of said peptides are polymerized.

3. The method according to claim 1 in which said modified peptides are from the same protein.

4. The method according to claim 1 in which said modified peptides are from various proteins.

5. The method according to claim 1 in which the antigen is a dimer comprising two different intrinsically disordered peptides which are cross-linked.

\* \* \* \* \*